United States Patent
Hands

(10) Patent No.: US 9,162,798 B2
(45) Date of Patent: Oct. 20, 2015

(54) BEVERAGE CAN INCLUDING ANTIMICROBIAL WIPE

(71) Applicant: Christopher Hands, Freehold, NJ (US)

(72) Inventor: Christopher Hands, Freehold, NJ (US)

(*) Notice: Subject to any disclaimer, the term of this patent is extended or adjusted under 35 U.S.C. 154(b) by 0 days.

(21) Appl. No.: 13/935,674

(22) Filed: Jul. 5, 2013

(65) Prior Publication Data

US 2014/0021202 A1 Jan. 23, 2014

Related U.S. Application Data

(60) Provisional application No. 61/672,314, filed on Jul. 17, 2012.

(51) Int. Cl.
*B65D 25/20* (2006.01)
*A01N 25/34* (2006.01)

(52) U.S. Cl.
CPC .............. *B65D 25/20* (2013.01); *A01N 25/34* (2013.01); *B65D 25/205* (2013.01); *B65D 2517/0056* (2013.01)

(58) Field of Classification Search
CPC ............. B65D 25/20; B65D 25/205; B65D 2517/0056; B65D 75/58; A01N 25/34; A47K 2010/3266; A47K 2010/3273; A47K 10/24
USPC ............. 220/87.1, 694, 735; 206/217, 831, 206/459.5; 15/104.93; 383/209, 207, 205, 383/208; 424/404
See application file for complete search history.

(56) References Cited

U.S. PATENT DOCUMENTS

| | | | | |
|---|---|---|---|---|
| 1,798,339 A * | 3/1931 | Soulis | ........................ | 206/217 |
| 2,292,413 A * | 8/1942 | Taylor | ........................ | 206/229 |
| 4,116,338 A * | 9/1978 | Weichselbaum | ........... | 206/438 |
| 4,332,319 A * | 6/1982 | Hurwood | ...................... | 206/210 |
| 4,651,890 A * | 3/1987 | Coker et al. | .................. | 220/694 |
| 4,775,094 A * | 10/1988 | Eisele | ............................. | 229/69 |
| 4,800,904 A * | 1/1989 | Kinseley et al. | ............. | 132/73.5 |
| 5,403,636 A * | 4/1995 | Crum | ........................... | 428/41.8 |
| 5,738,382 A * | 4/1998 | Grosskopf et al. | ............ | 283/81 |
| 5,837,338 A * | 11/1998 | Rich et al. | .................... | 428/42.3 |
| 5,996,169 A * | 12/1999 | Cooper | ...................... | 15/257.01 |
| 6,090,215 A * | 7/2000 | Cooper | .......................... | 134/6 |
| 6,322,864 B1 * | 11/2001 | Fresnel | ....................... | 428/34.9 |
| 6,383,504 B1 * | 5/2002 | Dotson | ........................ | 424/402 |
| 6,419,153 B1 * | 7/2002 | Maita | .......................... | 229/400 |
| 6,672,817 B2 * | 1/2004 | Denny | ......................... | 426/112 |
| 6,719,140 B1 * | 4/2004 | Rinsler | ....................... | 206/541 |
| 6,808,072 B2 * | 10/2004 | Snedeker et al. | ............ | 206/542 |
| 7,156,229 B2 * | 1/2007 | Gordon et al. | ............. | 206/308.1 |
| 7,686,161 B2 * | 3/2010 | Simmons | ...................... | 206/217 |
| 8,403,172 B1 * | 3/2013 | Kelley et al. | ................. | 220/710 |
| 8,549,676 B1 * | 10/2013 | Mandel | ........................ | 4/245.1 |
| 2002/0043473 A1 * | 4/2002 | Lee et al. | ...................... | 206/217 |
| 2004/0118431 A1 * | 6/2004 | Flynn | .......................... | 134/6 |
| 2004/0149598 A1 * | 8/2004 | Scarla | .......................... | 206/217 |
| 2006/0062832 A1 * | 3/2006 | Lopes | ......................... | 424/443 |
| 2006/0131188 A1 * | 6/2006 | Lindemann | ................... | 206/217 |
| 2010/0288781 A1 * | 11/2010 | Kelley et al. | ................. | 220/710 |
| 2011/0139784 A1 * | 6/2011 | Hemmerlin | .................. | 220/270 |
| 2011/0203069 A1 * | 8/2011 | Boorstein | ....................... | 15/247 |
| 2012/0132557 A1 * | 5/2012 | Nowzari | .................... | 206/459.5 |

* cited by examiner

*Primary Examiner* — Steven A. Reynolds
(74) *Attorney, Agent, or Firm* — Carla Gannon Law

(57) ABSTRACT

An improved beverage can includes a GRAS antimicrobial wipe contained in a low profile pouch that is adhered to the side of the can. The low profile pouch is constructed of a substantially planar substrate that retains the wipe directly to the exterior surface of the can. The pouch includes a perforated tab that is removed to access the wipe. To use, the perforated tab is ripped off, the user reaches into the pouch and pulls out the antimicrobial wipe, and wipes the can as desired, typically focusing on the drinking region of the can.

8 Claims, 4 Drawing Sheets

BEVERAGE CAN INCLUDING ANTIMICROBIAL WIPE

RELATED APPLICATIONS

This application claims the benefit of U.S. Provisional Patent Application 61/672,314, filed Jul. 17, 2012.

BACKGROUND OF THE INVENTION

1. Field of the Invention

The present invention relates to improved beverage cans, and more specifically to a beverage can having an antimicrobial wipe attached thereto.

2. Description of the Prior Art

It is very common for people to consume beverages directly out of cans, especially when they are away from home and it is not convenient to use a drinking vessel such as a glass. However, because the drinking surfaces of beverage cans are typically exposed in the manufacturing, transportation, packaging, and retail environments, there are simply no assurances that drinking from a beverage can is sanitary.

Some people try to lessen the potential contamination by wiping the drinking surface of their beverage can on a substrate such as clothing they are wearing, or possibly a paper towel. However, the actual effectiveness of this is questionable. In addition, it isn't always convenient or practical to wash the drinking surface of a beverage can with soap and water, especially when away from home.

As can be seen, there is a need for a system to quickly and efficiently decontaminate the drinking surface of a beverage can. It is desirable that this system is inexpensive and doesn't substantially alter the size, shape or weight of conventional beverage cans.

SUMMARY OF THE INVENTION

An improved beverage can includes a GRAS antimicrobial wipe contained in a low profile pouch that is adhered to the side of the can. The low profile pouch is constructed of a single substantially planar substrate that secures the wipe directly to the exterior surface of the can. The pouch is adhered to the can with one of the edges of the pouch having a perforated tab. To use, the perforated tab is ripped away, the user reaches into the pouch and pulls out the antimicrobial wipe, and wipes the can as desired, typically focusing on the drinking region of the can.

DETAILED DESCRIPTION OF THE PREFERRED EMBODIMENTS

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The following numbers apply to the following structures among the FIGS.:
1—Beverage can;
2—Adhesive;
3—Pouch
4—Pull away tab;
5—Antimicrobial wipe; and
6—Perforations.

Broadly, an embodiment of the present invention provides a beverage can having an antimicrobial wipe that is within a pouch adhered to the beverage can's outside.

Figure 1:
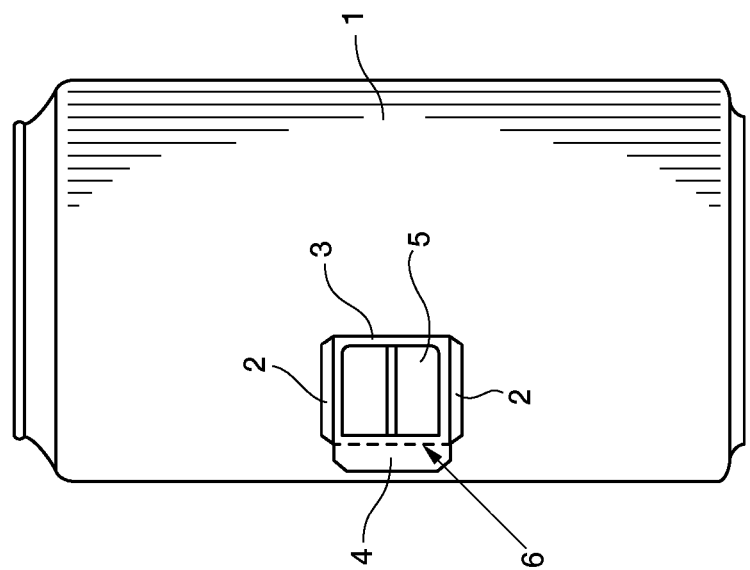
FIG. 1 is a front view of an embodiment of the present invention.
Figure 2:
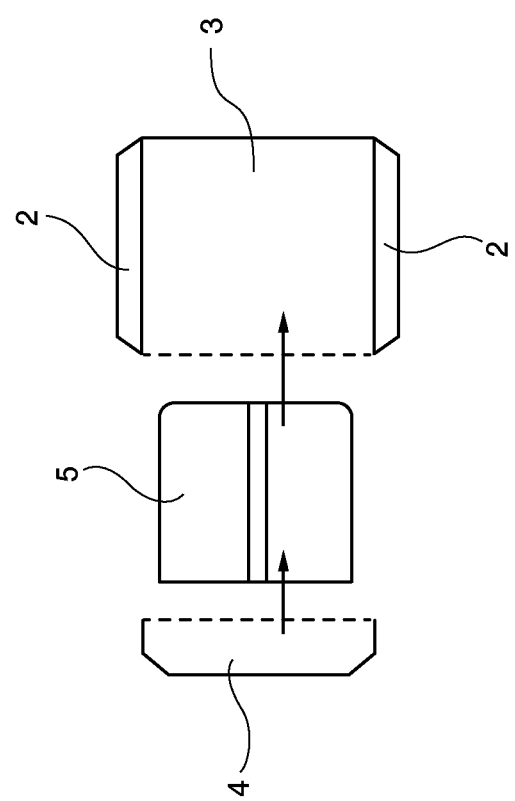
FIG. 2 is an exploded view of components of the present invention.

Referring to FIG. 1, an embodiment of the present invention includes beverage can 1, with pouch 3 adhered thereto. Beverage can 1 can be a variety of sizes and shapes, and contain a variety of beverages. Pouch 3 is desirably adhered directly to beverage can 1 by adhesive 2 along some or all of the edges of pouch 3. Pull away tab 4 desirably includes a plurality of perforations 6 which facilitate ripping open pouch 3, in order to access antimicrobial wipe 5 inside. An exploded view of one embodiment is depicted in FIG. 2.

It is desirable that pouch 3 is constructed of one, and only one, substantially planar substrate which is not folded or otherwise reshaped, such that pouch 3 including wipe 5 assumes a low profile (less than 5 mm, and preferably less than 3 mm) when adhered to can. This allows the transportation and distribution of beverage cans in the conventional manner. Pouch substrate preferably defines tab 4 having perforations 6. Adhesive 2 is present along edges of pouch, but not in a manner that would prevent access to wipe 5 upon removal of tab 4, or that would adhere wipe to pouch or underlying can.

In a preferred embodiment antimicrobial wipe 5 is constructed of a matrix impregnated with a GRAS antimicrobial. Wipe 5 may be folded within pouch 3. Suitable matrices include textiles, non-wovens, plastics, films, and composites. As used herein "GRAS" refers to those chemicals and substances that are designated by the US Food and Drug Administration (FDA) as "Generally Recognized As Safe", and therefore exempted from standard Federal Food, Drug, and Cosmetic Act (FFDCA) food additive tolerance requirements. Suitable GRAS antimicrobials include triclosan, propionic acid, propionates, benzoic acid, benzoates, diacetyl, proylgallate, sorbic acid, sorbates, esters of p-hydroxybenzoate (including methylparaben; propylparaben; butylparaben; ethylparaben; and heptylparaben), sulphur dioxide, sulphites, nitrites, nitrates, hydrogen peroxide, acetic and lactic acids, chlorine dioxide, methyl bromide, butylated hydroanisole, butylated hydroxytoluene, butylhydroquinoline, nordihydroguaiaretic acid, ethylenediamine tetractic acid, sodium citrate, lauric acid, monolaurin, diacetyl, d- and l-carvone, phenylacetaldehyde, methanol, vanillin, maltol, methanol, phenylacetic acid, 2,3-pentanedione, isoscorbate, allicin, allyl isothiocyanate, isothymol, cinnamic aldehyde, eugenol, thymol, sodium acid pyrophosphate, sodium triolyphosphate, sodium pyrophosphate, and any combination thereof.

It is desirable that antimicrobial wipe 5 is efficacious against Gram positive bacteria, Gram negative bacteria, viruses, molds, spores, and/or fungi. A wipe is deemed efficacious if >98% of the organisms are either killed or wiped off from 5 seconds of wiping.

Figure 3:
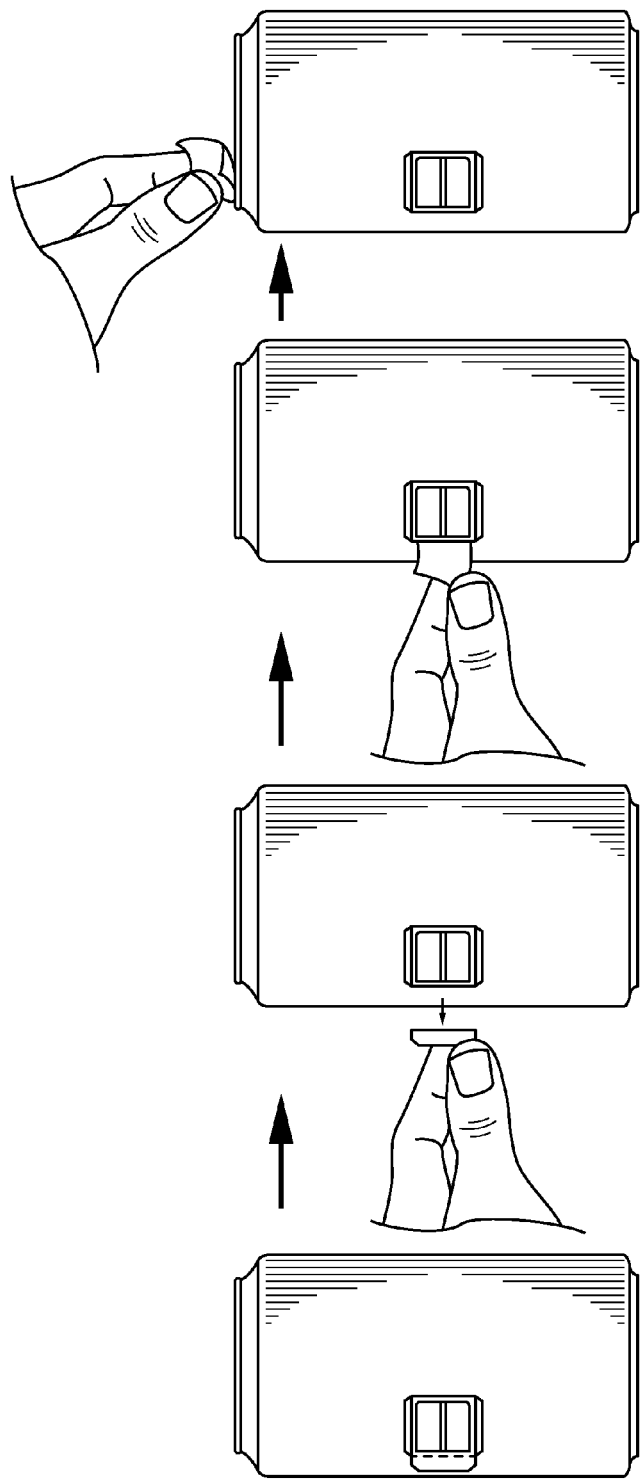
FIG. 3 depicts a method of practicing an embodiment of the present invention.
Figure 4:
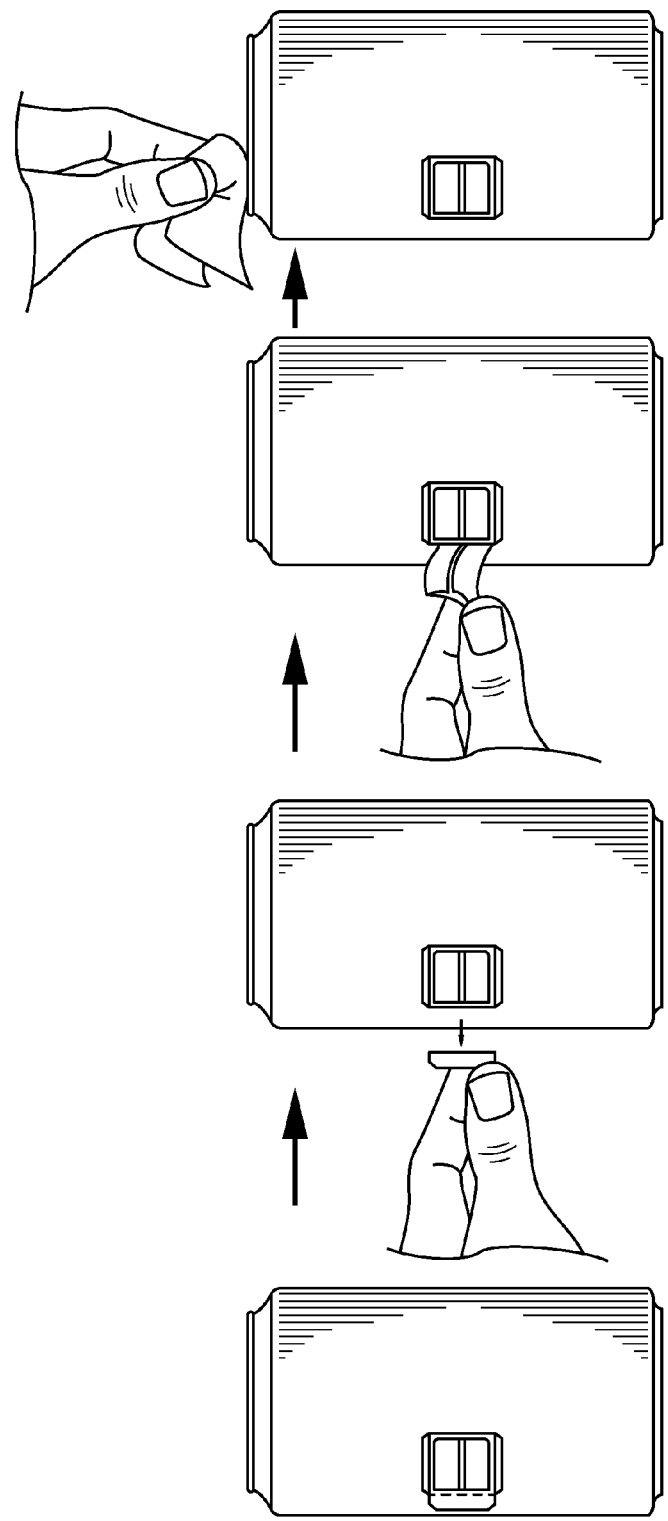
FIG. 4 depicts a method of practicing another embodiment of the present invention.

Use is depicted in FIGS. 3 and 4, with the former representing wipe 5 that is not folded, while the latter represents folded wipe 5 emerging from pouch. In use, one grasps and pulls non-adhesive pull away tab 4, thereby opening one edge of pouch 3. Then one obtains antimicrobial wipe 5 by reaching into pouch 3 and removing through open edge. A user then wipes the beverage can, desirably focusing on the drinking region of the can which includes the pour hole and surrounding area that contacts the mouth while drinking. If the wiping occurs before the can is opened, the portion of the beverage can obstructing the pour hole is desirably wiped. Wiping can also occur after beverage can is opened, and particularly between drinkers if multiple people are drinking from the same can. Antimicrobial wipe 5 can be stuffed back into the pouch for disposal alongside can.

It should be understood, of course, that the foregoing relates to exemplary embodiments of the invention and that modifications may be made without departing from the spirit and scope of the invention as set forth in the following claims. It should also be understood that ranges of values set forth inherently include those values, as well as all increments between. It should also be understood that "substantially" means within reasonable bounds considering human error and machine limitations. As used herein, "approximately" and the like shall mean+/−5%.

What is claimed is:

1. An improved drinking assembly including:
   a. a beverage can;
   b. a pouch adhered to said beverage can, said pouch having a substantially rectangular perimeter with at least two adhesive edges, and a non-adhesive region within said perimeter;
   c. a non-adhesive pull away tab adjoining one edge of said pouch, said pouch and said pull away tab separated only by a single perforation solely in a straight line, and
   d. an antimicrobial wipe within said pouch.

2. The drinking assembly of claim 1 wherein said pouch is constructed of a substantially planar substrate.

3. The drinking assembly of claim 2 wherein said substantially planar substrate is adhered along at least three edges to said beverage can.

4. The drinking assembly of claim 1 wherein the removal of said pull away tab exposes said one edge.

5. The drinking assembly of claim 4 wherein said one edge provides an access to said pouch when said pull away tab is removed.

6. The drinking assembly of claim 1 wherein said antimicrobial wipe includes a matrix impregnated with a GRAS antimicrobial.

7. The drinking assembly of claim 1 wherein said antimicrobial wipe is folded.

8. The drinking assembly of claim 1 wherein said pull away tab is outside said perimeter.

\* \* \* \* \*